United States Patent
Gravesen et al.

(10) Patent No.: US 8,945,064 B2
(45) Date of Patent: Feb. 3, 2015

(54) DEVICE FOR ADMINISTERING OF MEDICATION IN FLUID FORM

(75) Inventors: Peter Gravesen, Nordborg (DK); Per Brandt Rasmussen, Augustenborg (DK); Holger Dirac, Birkeroed (DK)

(73) Assignee: CeQur SA, Horw (CH)

( * ) Notice: Subject to any disclaimer, the term of this patent is extended or adjusted under 35 U.S.C. 154(b) by 238 days.

(21) Appl. No.: 12/195,791

(22) Filed: Aug. 21, 2008

(65) Prior Publication Data

US 2009/0054867 A1 Feb. 26, 2009

Related U.S. Application Data

(63) Continuation of application No. 10/503,845, filed as application No. PCT/DK03/00107 on Feb. 18, 2003.

(30) Foreign Application Priority Data

Feb. 18, 2002 (DK) .................................. 2002 00240
Jun. 25, 2002 (DK) .................................. 2002 00970

(51) Int. Cl.
*A61M 5/178* (2006.01)
*A61M 5/168* (2006.01)
(Continued)

(52) U.S. Cl.
CPC ........... *A61M 5/16881* (2013.01); *A61M 5/141* (2013.01); *A61M 5/14244* (2013.01);
(Continued)

(58) Field of Classification Search
USPC ........... 604/506, 150, 500, 522, 891.1, 890.1, 604/175, 9, 151, 123, 67
See application file for complete search history.

(56) References Cited

U.S. PATENT DOCUMENTS 3,895,741 A 7/1975 Nugent et al.
4,055,175 A 10/1977 Clemens et al.
(Continued)

FOREIGN PATENT DOCUMENTS

DE 42 00 595 7/1993
EP 0039124 A1 * 6/1981 .............. A61M 5/14
(Continued)

OTHER PUBLICATIONS

European Search Report for Application No. EP08013595 published Sep. 23, 2009.
(Continued)

*Primary Examiner* — Quynh-Nhu H Vu
*Assistant Examiner* — Brandy S Lee
(74) *Attorney, Agent, or Firm* — Goodwin Procter LLP

(57) ABSTRACT

An infusion device for continuous infusion of medication is disclosed, in which infusion is controlled over two separate fluid communications. The infusion is in each fluid communication controlled by restricting means and valve means, and one of the fluid communications further contains a holding device for bolus rate of infusion. The device comprises a flow regulating device comprising a passage defined by at least a first element and a second element, wherein at least one of the first and second element is a primary deformable element adapted to be elastically deformed so as to change the cross sectional area of the passage. Furthermore the device comprises a container for storage and supply of a medication in fluid form, said container comprising a first and a second chamber being arranged relatively to each other so that when volume of the first chamber increases the volume of the second chamber decreases.

13 Claims, 5 Drawing Sheets

(51) Int. Cl.
*A61M 5/14* (2006.01)
*A61M 5/142* (2006.01)
*A61M 5/148* (2006.01)
*A61M 5/152* (2006.01)

(52) U.S. Cl.
CPC .......... *A61M5/14276* (2013.01); *A61M 5/148* (2013.01); *A61M 5/16804* (2013.01); *A61M 5/152* (2013.01); *A61M 5/16813* (2013.01); *A61M 5/16854* (2013.01); *A61M 2005/1405* (2013.01); *A61M 2205/0244* (2013.01); *A61M 2205/0294* (2013.01); *A61M 2205/3306* (2013.01); *A61M 2205/3331* (2013.01)
USPC ............................ 604/183; 604/131; 604/132

(56) References Cited

U.S. PATENT DOCUMENTS

| | | | |
|---|---|---|---|
| 4,077,405 A | 3/1978 | Haerten et al. | |
| 4,193,397 A | 3/1980 | Tucker et al. | |
| 4,209,014 A | 6/1980 | Sefton et al. | |
| 4,265,241 A | 5/1981 | Portner et al. | |
| 4,431,425 A | 2/1984 | Thompson et al. | |
| 4,443,218 A | 4/1984 | DeCant, Jr. et al. | |
| 4,447,224 A | 5/1984 | DeCant, Jr. et al. | |
| 4,486,190 A | 12/1984 | Reinicke | |
| 4,525,165 A | 6/1985 | Fischell | |
| 4,557,726 A | 12/1985 | Reinicke | |
| 4,569,675 A | 2/1986 | Prosl et al. | |
| 4,575,041 A | 3/1986 | Hu | |
| 4,604,089 A | 8/1986 | Santangelo et al. | |
| 4,671,320 A | 6/1987 | Grifols Lucas et al. | |
| 4,714,462 A | 12/1987 | DiDomenico | |
| 4,715,852 A | 12/1987 | Reinicke et al. | |
| 4,730,635 A | 3/1988 | Linden | |
| 4,755,173 A | 7/1988 | Konopka et al. | |
| 4,820,273 A | 4/1989 | Reinicke | |
| 4,868,585 A | 9/1989 | Nishikawa et al. | |
| 4,886,499 A | 12/1989 | Cirelli et al. | |
| 4,931,050 A | 6/1990 | Idriss | |
| 4,994,035 A | 2/1991 | Mokros | |
| 4,998,918 A | 3/1991 | Mimura et al. | |
| 5,011,477 A | 4/1991 | Winchell et al. | |
| 5,033,714 A | 7/1991 | Winchell et al. | |
| 5,085,644 A | 2/1992 | Watson et al. | |
| 5,088,983 A | 2/1992 | Burke | |
| 5,152,753 A | 10/1992 | Laguette et al. | |
| 5,176,358 A | 1/1993 | Bonne et al. | |
| 5,176,662 A | 1/1993 | Bartholomew et al. | |
| 5,178,609 A | 1/1993 | Ishikawa et al. | |
| 5,192,272 A | 3/1993 | Faure et al. | |
| 5,211,632 A | 5/1993 | Tsukada et al. | |
| 5,224,934 A | 7/1993 | Payne et al. | |
| 5,241,985 A | 9/1993 | Faust et al. | |
| 5,248,301 A | 9/1993 | Koenig, Jr. et al. | |
| 5,257,980 A | 11/1993 | Van Antwerp et al. | |
| 5,304,153 A | 4/1994 | Tsujikawa et al. | |
| 5,346,372 A | 9/1994 | Naruse et al. | |
| 5,575,770 A * | 11/1996 | Melsky et al. | 604/288.04 |
| 5,584,813 A | 12/1996 | Livingston et al. | |
| 5,762,632 A | 6/1998 | Whisson et al. | |
| 5,839,467 A | 11/1998 | Saaski et al. | |
| 5,851,197 A | 12/1998 | Marano et al. | |
| 5,857,661 A | 1/1999 | Amada et al. | |
| 5,871,478 A | 2/1999 | Berrigan | |
| 5,925,017 A * | 7/1999 | Kriesel et al. | 604/132 |
| 5,931,814 A | 8/1999 | Alex et al. | |
| 5,961,488 A | 10/1999 | Barak et al. | |
| 5,993,425 A | 11/1999 | Kriesel | |
| 5,997,501 A | 12/1999 | Gross et al. | |
| 6,045,533 A | 4/2000 | Kriesel et al. | |
| 6,068,751 A | 5/2000 | Neukermans | |
| 6,090,068 A | 7/2000 | Chanut et al. | |
| 6,213,151 B1 | 4/2001 | Jacobson et al. | |
| 6,406,276 B1 | 6/2002 | Normand et al. | |
| 6,416,495 B1 | 7/2002 | Kriesel et al. | |
| 6,471,675 B1 | 10/2002 | Rogers et al. | |
| 6,485,461 B1 | 11/2002 | Mason et al. | |
| 6,579,267 B2 | 6/2003 | Lynch et al. | |
| 6,585,707 B2 | 7/2003 | Cabiri et al. | |
| 6,607,509 B2 | 8/2003 | Bobroff et al. | |
| 6,620,138 B1 | 9/2003 | Marrgi et al. | |
| 6,620,151 B2 * | 9/2003 | Blischak et al. | 604/891.1 |
| 6,666,845 B2 | 12/2003 | Hooper et al. | |
| 6,669,669 B2 | 12/2003 | Flaherty et al. | |
| 6,702,779 B2 | 3/2004 | Connelly et al. | |
| 6,730,060 B1 | 5/2004 | Steinbach et al. | |
| 6,749,587 B2 | 6/2004 | Flaherty | |
| 6,802,823 B2 | 10/2004 | Mason | |
| 6,830,562 B2 | 12/2004 | Mogensen et al. | |
| 6,926,694 B2 | 8/2005 | Marano-Ford et al. | |
| 6,936,026 B2 | 8/2005 | Diermann et al. | |
| 6,960,192 B1 | 11/2005 | Flaherty et al. | |
| D515,288 S | 2/2006 | Della Valle et al. | |
| 6,997,907 B2 | 2/2006 | Safabash et al. | |
| 7,207,345 B2 | 4/2007 | Somerville | |
| 7,207,974 B2 | 4/2007 | Safabash et al. | |
| 2002/0087147 A1 | 7/2002 | Hooper et al. | |
| 2003/0216683 A1 * | 11/2003 | Shekalim | 604/67 |
| 2004/0059316 A1 | 3/2004 | Smedegaard | |
| 2004/0249363 A1 | 12/2004 | Burke et al. | |
| 2005/0101932 A1 | 5/2005 | Cote et al. | |
| 2005/0124936 A1 | 6/2005 | Mogensen et al. | |
| 2005/0255003 A1 | 11/2005 | Summersgill et al. | |
| 2005/0266582 A1 | 12/2005 | Modlin et al. | |
| 2005/0267441 A1 | 12/2005 | Douglas | |
| 2006/0264835 A1 | 11/2006 | Nielsen et al. | |
| 2007/0299397 A1 | 12/2007 | Alferness et al. | |
| 2008/0119822 A1 | 5/2008 | Knauper | |
| 2008/0183060 A1 | 7/2008 | Steil et al. | |

FOREIGN PATENT DOCUMENTS

| | | |
|---|---|---|
| EP | 0 039 124 | 11/1981 |
| EP | 0 239 721 | 7/1987 |
| EP | 0427588 | 5/1991 |
| EP | 0 239 244 | 9/1991 |
| EP | 0450186 A1 | 10/1991 |
| EP | 0 562 694 | 9/1993 |
| EP | 0 646 381 | 4/1995 |
| EP | 0 960 626 | 12/1999 |
| EP | 1254676 A1 | 11/2002 |
| GB | 1029233 A | 5/1966 |
| GB | 2 031 558 | 4/1980 |
| GB | 2 197 691 | 5/1988 |
| JP | 56-136562 | 10/1981 |
| JP | 63-197464 | 8/1988 |
| JP | 3-165872 | 7/1991 |
| JP | 5-15590 | 1/1993 |
| JP | 8-206199 | 8/1996 |
| RU | 2129021 C1 | 4/1999 |
| WO | WO-92/16304 | 10/1992 |
| WO | WO-93/05832 A1 | 4/1993 |
| WO | WO-97/12665 A1 | 4/1997 |
| WO | WO-99/27985 | 6/1999 |
| WO | WO-99/44655 | 9/1999 |
| WO | WO-99/44740 A1 | 9/1999 |
| WO | WO-01/85233 | 11/2001 |
| WO | WO-02/070047 | 9/2002 |
| WO | WO-2006/032692 | 3/2006 |

OTHER PUBLICATIONS

International Search Report for International Application No. PCT/DK03/00107 mailed on Jan. 10, 2003.

* cited by examiner

DEVICE FOR ADMINISTERING OF MEDICATION IN FLUID FORM

CROSS-REFERENCE TO RELATED APPLICATIONS

This application is a continuation of and incorporates by reference herein in its entirety U.S. patent application Ser. No. 10/503,845, filed Feb. 25, 2005, entitled "Device for Administering of Medication in Fluid Form," which is entitled to the benefit of International Patent Application No. PCT/DK03/00107, filed on Feb. 18, 2003; Danish Patent Application No. PA 2002 00240, filed on Feb. 18, 2002; and Danish Patent Application No. PA 2002 00970 filed on Jun. 25, 2002, the disclosures of which are hereby incorporated by reference herein in their entireties.

FIELD OF THE INVENTION

The present invention relates to a device for administering a medication and more specifically to a safe construction for administering a medication in fluid form and in particular to a device for administering a medication with a sensitive structure. Furthermore the present invention relates to valve and in particular to a valve suitable for administering small doses of a fluid.

BACKGROUND OF THE INVENTION

Administering systems for continuous administering of a medication in fluid form are known in the art, and used in hospitals. The purpose for such devices is to give the patient the freedom of movement, even though he is connected to a device for administering of a medication e.g. by infusion. The adjustment of the rate of discharge from such devices takes place only by adjusting the dosage by hand, and is done by the personnel at the hospital as a part of the treatment of the patient.

Administering systems for controlled administering of fluid based medication, outside hospitals is also known in the art. Such systems may work by moving a piston in controlled steps, leading to infusion in batches. A plurality of pump devices for administering of insulin to diabetic patient used to day is based on infusion in controlled steps. The medication is administered into tissue, from which the medication diffuses into the blood.

SUMMARY OF THE INVENTION

It is an object of the present invention to provide a device for continuous administering of fluid based medication, wherein the administering is controllable, and where the infusion during any fault situation in the device is unable to harm the patient.

A further object of the present invention may be to provide a device which may be able to administer medication in two types of doses—a basal dose and a bolus dose. Furthermore it may be an object of a preferred embodiment of the present invention to provide a device wherein the flow of medication in the device may be monitored.

According to a first aspect the present invention relates to a device for administering of a medication in fluid form, said device comprising an outlet means and a storage means for storage of a fluid, said device further comprising, two individual communications each of which being in fluid communication with the storage means and the outlet means, each communication comprising at least one flow restricting means, at least one valve means arranged down stream the storage means and upstream at least one flow restricting means, and wherein at least one of said individual communications comprises a holding means intermediate the storage means and the valve means, said holding means being in fluid communication with said storage means over at least one restriction means.

The fluid of the device may contain a medication or may be any other fluid such as a saline solution. The device may be adapted to restrict the rate at which a medication is administered e.g. discharged thought the outlet of the device. The outlet may be connected to a cannula or to a tube connected to a cannula.

At least a part of the device may be adapted to be positioned in a body of a mammal e.g. a human being, for shorter or longer period. In some embodiments only a cannula is placed in the human body and the rest of the device is placed outside the body. In some embodiments the storage means may be adapted for accommodation in a human body and thus refilling of the storage means may be done by means of a needle inserted through the skin of the human being or mammal.

The medication comprised in the fluid may be insulin or hormones or an anti-inflammatoric medication. The two communications may be in individual fluid communication with the storage means and the outlet means. In some embodiments a part of each of the two communications may be provided by the same tube such that said tube branches out into two separate communications. The two communications may branch out and merge in different locations on the individual communications.

The restriction means may be provided by small tubes e.g. capillaries adapted to restrict the flow. In an embodiment all restricting means are provided as capillaries. The capillaries may have different internal diameters so as to allow different flow rates. In an embodiment at least one of the capillaries is provided by a piezoelectric element adapted to change the internal diameter such that the flow rate of said capillary may be Varied. Such a piezoelectric element may be annular.

The cross-sectional area of at least one of the capillaries may be between 10 µm$^2$ and 50 µm$^2$, such as between 15 µm$^2$ and 30 µm$^2$ such as 20 µm$^2$. The length of the capillaries may be used to design the desired pressure drop over the capillary. Thus the small capillaries of the present invention e.g. the capillary used for the basal dose, may have a length of between 30 mm and 100 mm, such as between 40 mm and 80 mm, such as between 50 mm and 70 mm, such as 66 mm. In order to reduce the physical extend of the capillary the capillary may be U-shaped or define any other shape reducing the physical extend of the capillary.

The length of the larger capillary e.g. the capillary upstream of the holding means may be 3-10 times shorter than the aforementioned capillary, such as between 5 and 8 times shorter. The length of the capillary may be adapted to the individual person who uses the device. The size of the capillary may be chosen with regard to data of the person such as size, weight, metabolism, the average size of meals eaten by the person etc.

In an embodiment the capillaries may be provided in units having lengths of 10 mm such that joining the capillaries in series may provide a desired length. Thus the ends of units may be adapted for attachment to each other. According to the first aspect of the invention the capillaries and the valve means may be provided in a surface of a substrate comprising silicon. Thus the first and/or the second individual communication may be provided in the silicon substrate.

The invention according to the first aspect may comprise one valve. The valve may be arranged in one of the two communications or a valve may be provided in each of the two communications. By providing a valve it may be possible to control the administering of medication even more precisely as the flow in one or both of the individual communications may be shut off and turned on in any desired pattern.

In the present application a restriction means is defined as a means for restricting the flow rate. A restriction means may vary the flow rate and thus be adjustable.

In the present application a valve means is defined as a means which is able to shut off the flow completely. Thus a valve may be set in any position between two opposite positions, the open position and the closed position i.e. valve may be set in any intermediate position. A valve may thus be seen as a restriction means which can be shut off.

In the present invention a communication is defined as any path wherein a fluid may flow.

At least one of the individual communications comprises a holding means. Said holding means may be adapted to store a predetermined amount of medication of fluid such that a larger dose of medication or fluid may be administered. In some embodiments, both the individual communications may comprise separate holding means such that each of the two communications may be used for administering a larger dose. Thus if the two individual communications provide passage for different types of medications, larger doses of each of the two medications may be administered individually. As an example, one of the two communications may be in fluid connection with fluid comprising insulin, while the other communication is in fluid communication with a glucose solution. Should an overdose of insulin be administered, the holding member of the communication providing passage for glucose may be used to eliminate the undesired effects of the overdose. The two communications may provide passage for any complementary medications.

The device may comprise means for pressurising said storage means. Such means may be an elastic member provided around the storage means. In other embodiments the means for pressurising may be provided as electrically actuated actuation means or a pressure compartment adapted to apply a pressure on the storage means.

It may be desirable to be able to monitor the administering of medication. Thus at least one of said restricting means may comprise detection means adapted to supervise the flow in the restricting means. The detection means may be an impeller or any other device for supervising a flow. In an embodiment the detection means may be adapted to detect a pressure difference between a supply-side and a discharge-side of the restriction means.

The supply-side may in some embodiments be seen as directly at the inlet, while in other embodiments the supply-side may be seen as an area in the vicinity of the inlet. In yet other embodiments the supply-side may be seen as anywhere between the inlet and another element in the communication e.g. the first upstream element.

The discharge-side may in some embodiments be seen as directly at the outlet, while in other embodiments the discharge-side may be seen as an area in the vicinity of the outlet. In yet other embodiments the discharge-side may be seen as anywhere between the outlet and another element in the communication e.g. the first downstream element.

In some embodiments only some of the restriction means are provided with a detecting means whereas in other embodiments all restriction means are provided with detection means.

As the flow is monitored it may be possible for a control means to monitor the amount of medication or fluid which is administered.

The detection means may comprise a membrane adapted to move between a first position and a second position, each side of said membrane may be in fluid communication with an inlet and/or an outlet of a restricting means. Thus the position of the membrane may be used as an indicator for the pressure difference between the first and the second position.

In some embodiments at least one of the detection means may be arranged such that the pressure difference over two restriction means and/or valves may be determined. In other embodiments each detecting means may be in fluid communication with a supply-side and a discharge-side of one of the restricting means, such that the pressure difference over one restriction means is determined.

It may be desirable that the fluids on each side of the membrane are not in fluid connection. Thus the membrane may define a seal between a supply-side-chamber and a discharge-side-chamber. The supply-side-chamber and/or the discharge-side-chamber may be part of the detection means. In some embodiments the discharge-side-chamber of a first detection means may be a supply-side-chamber of a second detection means or vice versa. In order to determine the pressure difference between the two chambers, the membrane may comprise an elastic material. Such a material may comprise a natural rubber material and/or a synthetic rubber material.

As the medication to be administered may have a molecule structure which is so fragile that it may not be passed through the restriction means the device may comprise a separate container for storage and supply of a medication in fluid form. Said container may comprise a fluid chamber and a medication chamber being arranged relatively to each other so that when volume of the fluid chamber increases the volume of the medication chamber decreases. The container may comprise any feature or element of the second aspect of the present application.

The container may be arranged downstream at least one restriction means and upstream the outlet means. In one embodiment the container may be arranged downstream all the restriction means and upstream the outlet means. In the latter embodiment the fluid chamber may be in fluid communication with any restriction means and outlet means may be in communication with the medication chamber.

An advantage of the above mentioned container may be seen as eliminating any passing of the medication through a restriction means. Thus any other fluid e.g. a saline solution may be used to pressurise the medication chamber of the container.

In one embodiment the two individual communications may define a first and a second communication and wherein the first communication may be adapted for administering of a basal rate medication and the second communication may be adapted for administering of a bolus rate of medication. As the second communication is adapted for dosing of a bolus rate of medication it may comprise the holding means. Thus while the valve is closed the holding means may be filled up and as a restriction means may be provided upstream the holding means the filling rate may be low. When the valve is opened and the holding means is emptied the bolus rate of medication may be administered.

The holding means may comprise a chargeable accumulator adapted to be charged with fluid.

At least one of the aforementioned valve means may comprise:
a passage defined by at least a first element and a second element, wherein at least one of the first and second element is adapted to be elastically deformed so as to change the cross sectional area of the passage. In some embodiments all the valves of the device are made according to the above-mentioned description. Said valves may comprise any feature or element of the third aspect of the present invention.

In an embodiment of the first aspect of the present application the device may further comprise control means adapted to control the administering of medication. Such a control means may comprise a first computer system, the computer system comprising input means for collecting data in a first format, processing means for processing the data, output means for presenting data in a second format, and data storage means having stored therein a computer program.

The computer system may comprise an operating system. The data collected in the first format may be data from the detection means indication as to whether or not the flow in the system is according to the specification. The data in the first format may be information e.g. provided by the user, about administering of the bolus rate and/or the basal rate.

The data in the second format may be an alarm signal indicating that one of the restriction means and/or one of the valves is out of order. The data in the second format may be control information used to control the valve and/or the holding means. Accordingly in some embodiments the control means may be adapted to control the storage means and/or the holding means and/or at least one valve of the device for administration.

The control means may by operable by means of a separate control unit in wired and/or wireless connection with the device.

The computer program may be adapted to perform the steps of: a opening of the valve means in the second communication applying a pressure on the holding means so as to administer the bolus rate dosing the valve means in the second communication.

Furthermore the computer program may be adapted to remove the pressure on the holding means, so as to allow said means to be filled with a new bolus rate.

According to the first aspect of the invention medication may be infused at a rate controlled by one of the two communications, and the holding means may give the possibility of infusing a bolus rate of medication for a short period. The continuously rate of infusion the device is able to discharge, in case of all control are lost, is balanced to the patient, whereby the worst case fault situation is unable to harm the patient.

The restricting means of the infusion device may be supplied with detection means, supervising the infusion of medication. Hereby may be achieved that the control system receives information to evaluate the infusion situation, and hereby may be able to detect an infusion failure.

In a specific embodiment of the invention, a membrane may form the detection means, where each side of the membrane may be in fluid communication with each side of the restricting means. Hereby may be achieved that the direction of the deflection of said membrane may indicate the direction of pressure over said restricting means.

In another specific embodiment of the invention, separate pressure detectors may form detection means, each may be in pressure communication with supply side or discharge side of one of said restriction means. Hereby is achieved that the pressure detection can take place locally in the infusion communication pad, without any additional fluid communications being needed.

A membrane on the detecting means may seal a closed area comprising liquid, and an elastic element may give the membrane and the liquid the possibility of moving in accordance with a pressure rise on the side of the membrane facing away from said liquid, and the movement of liquid may be detectable. Hereby may be achieved that the medication may be kept inside the infusion communication, and only the pressure may be transported, via the membrane, to the liquid. This gives access to different ways for detecting the movement of the liquid, as no considerations regarding the impact from the medications itself has to be taken, besides from the choice of membrane material.

In a further specific embodiment, capillaries may form the restricting means in the infusion device. Hereby may be achieved that the rate of infusion may be well defined in relation to the pressure acting on each side of a restricting means.

The infusion device may contain storage means for medication, this storage means for medication may be pressurised by fluid from a separate part of the infusion device, whereby the rate at which medication discharge through the outlet means may depend on the rate at which fluid pressurises the storage means for medication. Hereby may be achieved that the medication may be infused directly from the storage compartment to the outlet of the infusion device, without passing any valves and restricting means. For sensitive medications this could be an advantage.

In a specific embodiment of the invention, one of the two individual communications may restrict the rate at which medication from one storage means for medication discharges, and the other of the two individual communications may restrict the rate at which medication from another storage means for medication discharges. Hereby may be achieved that medication of different strength or different response time may be discharged from the device.

It may be seen as an advantage that the two individual communications may form a first communication for basal rate of infusion of medication and a second communication for bolus rate of infusion of medication, and where the holding means may be contained in the second communication. The medication may hereby be able to infuse at controlled rates, depending on the actual and present need.

In an embodiment the first aspect of the present invention may relate to a device for infusion of medication, said device containing:
  storage means for storage of fluid,
  outlet means for infusion of medication,
  means for pressurising said storage means,
  means for restricting the rate at which medication discharge through said outlet means,
  valve means disposed intermediate said storage means and said restricting means, wherein two individual communications expose separate means for restricting the rate at which medication discharge through said outlet means, and in that one of said individual communications contains holding means intermediate said storage means and said valve means, said holding means being in fluid communication with said storage means over separate restriction means.

Said restricting means may be supplied with detection means, whereby infusion of medication is supervised.

Said detection means may be formed by a membrane, each side of said membrane being in fluid communication with each side of said restricting means, whereby the direction of the deflection of said membrane will indicate the direction of pressure over said restricting means.

The separate pressure detectors may form said detection means, each in pressure communication with supply side or discharge side of one of said restriction means.

A membrane may seal a closed area containing liquid, and that an elastic element may give said membrane and said liquid the possibility of moving in accordance with a pressure rise on the side of the membrane facing away from said liquid, said moving of liquid being detectable.

Said restricting means may be formed by capillaries.

Said fluid in said storage means may be the medication.

The device may contain storage means for medication, said storage means for medication being pressurised by fluid from said storage means for fluid, whereby the rate at which medication discharges through said outlet means may depend on the rate at which fluid pressurizes said storage means for medication.

One of said two individual communication may restrict the rate at which medication from one storage means for medication discharges, and the other of said two individual communication may restrict the rate at which medication from another storage means for medication discharge.

Said two individual communications may form a first communication for basal rate of infusion of medication and a second communication for bolus rate of infusion of medication, and where said holding means may be contained in said second communication.

Said holding means may form a chargeable accumulator, charge with fluid from said storage means over said separate restriction means, while said valve means in second communication is closed.

An opening of said valve means in said second communication may allow said holding means to perform said bolus rate of infusion of medication, while said holding means depressurise through said valve means in second communication, where after the rate of infusion of medication in said second communication may drop to a lower level controlled by said separate restriction means.

Said valve means may be formed by an elastomer material, which under actuation from an actuator will deform into a part of said communication, whereby flow of fluid may be prevented.

The invention according the first aspect of the invention may comprise any feature or element of the second and/or third aspect of the invention.

According to a second aspect the present invention relates to a flow regulating device comprising:

a passage defined by at least a first element and a second element, wherein at least one of the first and second element is a primary deformable element adapted to be elastically deformed so as to change the cross sectional area of the passage.

In some embodiments the first element is a primary deformable element, while in others the second element is a primary deformable element. Yet in other embodiments both the first and the second elements are primary deformable elements. In the latter case a half circle may be defined in both the elements such that the two half circles together define a circle. When the two elements are deformed the cross-sectional area of the circle may be deformed.

The primary deformable elements may be adapted to be changed between two positions a first position wherein the cross-sectional area is as big as possible and a second position wherein the cross-sectional area is as small as possible e.g. close to zero.

In an embodiment at least a part of the primary deformable element in the first position encircles at least a part of the passage.

When force is applied to the deformable element, the element may change from the first position to the second position or any intermediate position. Thus the force applied to the deformable element may be used to control the cross-sectional area of the passage.

In some embodiments a force in the direction of the centre of the passage may be applied in order to change the cross-sectional area of said passage. In other embodiments forces may applied on two sides of the primary deformable element. A force zone may then be defined between the forces and in some embodiments the passage may not be defined in the force zone. Thus the primary deformable element may be deformed in a first direction when a force is applied in a second direction, the first direction being transverse to the second direction.

A secondary deformable element may encircle the primary deformable element. The secondary deformable element may be harder than the primary deformable element. Thus the secondary deformable element may be adapted to work as an outer wall of the primary element. The secondary deformable element may in some embodiments be hard enough to retain its shape without any support from other elements. In other embodiments the secondary deformable element may not be hard enough to retain its shape without any support and therefore a supporting element may be provided around the second deformable element The softer the primary element is the easier it may be for the element to block the passage. In some embodiments the primary deformable element may be an oil or water or air. In some embodiments the primary and/or the secondary element may comprise an elastomer e.g. silicone. When choosing the elastomer it is essential that the elastomer and the medication may work together without damaging each other.

A membrane may be provided between the first and the second elements. Such a membrane may be adapted to provide a seal such that the primary element and/or the secondary element may not come in contact with the content of the passage e.g. a medication in fluid form. Thus the membrane may provide a seal between the first and the second elements. The membrane may comprise a natural rubber material and/or a synthetic rubber material.

The area of the passage may be between 0.1 mm$^2$ and 1 mm$^2$, such as between 0.25 mm$^2$ and 0.5 mm$^2$, such as between 0.25 mm$^2$ and 0.5 mm$^2$. It may be desirable to choose a cross-sectional area at any place of the individual communications, that is as small as possible, as the total volume in the two individual communications may then be limited. The smaller the total volume of the individual communications, the easier it may be to control the system. On the other hand, the cross-sectional areas may not be so small that the resistance in the system is too big. Only in the restriction means may the resistance be desired to be small.

According to the second aspect of the invention a device may be provided in which a valve means may be formed by an elastomer material, which under actuation from an actuator may deform into a part of said communication, whereby flow of fluid may be prevented.

The invention according to the second aspect of the present invention may comprise any feature or element of the first and/or third aspect of the invention.

According to a third aspect the present invention relates to a container for storage and supply of a medication in fluid form, said container comprising a first and a second chamber being arranged relatively to each other so that when volume of the first chamber increases the volume of the second chamber decreases.

In an embodiment the first chamber and the second chamber are interconnected by a hydraulic system e.g. comprising a saline solution. Thus the hydraulic liquid may be used to change the volumes of the two chambers e.g. by moving pistons in each chamber.

Furthermore at least a part of a sidewall separating the first and second chamber may movable. Thus in one embodiment only one wall separates the first and the second chamber and said wall may work as a piston.

In other embodiments at least a part of a sidewall separating the first and second chamber may be flexible. Thus a bag-like element defining the secondary chamber may be provided in a large chamber. The part of the large chamber, which is not filled with the bag-like element, may define the primary chamber. When the primary chamber is filled with a fluid the secondary chamber in the bag-like element collapses and fluid in the bag may be administered. In some embodiments the bag-like element defines the primary chamber and the rest of the large chamber defines the secondary element.

The first chamber may be a fluid chamber adapted for storage of a fluid e.g. a saline solution and the second chamber may be a medication chamber for storage of medication. The saline solution may be an isotonic solution which does not change the balance of salts on the blood.

In general it may be seen as an advantage to choose elements and fluids which does not damage each other and which may be inserted or administered in the human body.

The third aspect of the present invention may comprise any feature or element of the first and/or second aspect of the present invention.

BRIEF DESCRIPTION OF THE DRAWINGS

An embodiment of the invention will now be described in details with reference to the drawing in which.

DETAILED DESCRIPTION OF THE PREFERRED EMBODIMENTS

Figure 1:
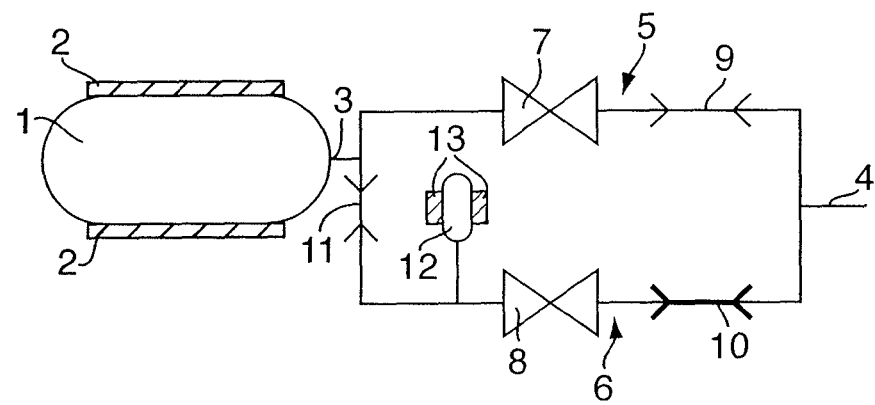
FIG. 1 shows a device according to the first aspect of the invention.

In FIG. 1 is shown an infusion device for administering of medication in fluid form, e.g. infusion of insulin to a diabetic patient. The device comprises a storage compartment 1, in which the medication is contained. The storage compartment 1 is made as a sealed bag with an outlet 3, through which medication can be discharged from the bag simply by adding a force external to the sides of the bag.

The compartment 1 is surrounded by an elastomer pressure jacket 2, which will apply a nearly constant force to the compartment, until being empty of medication. The pressure of the medication at the outlet 3 is hereby held constant, until the compartment 1 is emptied for medication. The outlet 3 is in connection with an outlet 4 from the device, from where the medication is administered e.g. infused.

The outlet 4 is in fluid communication with the compartment 1 over two individual communications 5 and 6, each having a valve 7 and 8 and a capillary 9 and 10. The capillary 9 has a small diameter, which will correspond to a low rate of discharge of medication, referred to as the basal rate. For diabetic patients this corresponds to the low rate of insulin discharge, which will balance the glucose level under normal conditions between meals. Adjustment of rate of discharge through capillary 9 can take place by adjustment of the valve 7. In some embodiments the valve 7 may be controlled between a fully open and a fully closed position, like a pulse modulation with adjustable duty rate in a fixed duty cycle. A high duty rate will then correspond to a high rate of discharge, however still within the basal rate.

The capillary 10 in communication 6 has a diameter larger than the diameter of the capillary 9. Thus the capillary 10 is able to discharge medication at a rate referred to as the bolus rate. For diabetic patients this corresponds to the high rate of insulin discharge, which will balance the glucose level during and right after meals. Adjustment of rate of discharge through capillary 10 can take place by adjustment of the valve 8. In some embodiments the valve 8 may be controlled between a fully open and a fully closed position, like a pulse modulation with adjustable duty rate in a fixed duty cycle. A high duty rate will then correspond to a high rate of discharge, and a low duty rate to a low rate of discharge, however still within the bolus rate.

In case of a valve failure of valve 7, causing the valve to jam in open position, the control of the basal rate will be lost. This may, related to infusion of insulin, cause a slightly over dosing of insulin between the meals, but will have no harmful effect on the diabetic patient. If the failure however was on valve 8, still jam in open position, the bolus rate of discharge will have a deadly effect on the diabetic patient.

In order to prevent the bolus rate of discharge to be uncontrolled, the communication 6 comprises a separate capillary 11, which will restrict the rate of discharge from compartment 1 through communication 6 to outlet 4, in case the valve 8 is jam in open position. The effect of the valve 8 being jam in open position will now be an uncontrolled bolus rate of discharge, but restricted to a low value. The capillary 11 may restrict the rate of discharge to a value correspond to the normal bolus infusion over a day, if this was to be infused continuously.

Under normal operation of the communication 6, valve 8 will be closed for a long period between the meals. In this period medication discharge from compartment 1, through capillary 11 to compartment 12, which is a small sealed bag in fluid communication with compartment 1, and with an elastomer pressure jacket 13, surrounding the compartment 12. This compartment 12 with pressure jacket 13 is referred to as a holding device, and works as an accumulator in hydraulic systems. The pressure in compartment 1 and compartment 12 will equalise during the close period for valve 8, and as valve 8 is opened the bolus rate of discharge will be high, as only capillary 10 restricts the rate of discharge from compartment 12 to outlet 4 in FIG. 1.

A valve failure will have an uncontrolled rate of discharge as result, but the rate of discharge will be restricted to a normal level of infusion over a day. The patient might feel a slightly uncomfortably, but will in no way be harmed by the valve failure.

The device of FIG. 1 is a wet disposable device, containing the medication in fluid form (e.g. insulin), the tubing, the capillaries, the valves and the holding device. The wet disposable device may contain other needed elements of the infusion device, such as actuating means for the valves and the elastomer pressure jackets. As the wet device is disposable, all elements, which are not in direct contact with the medication, could be contained in a control device, and the control device and the wet device could be connected in a way that makes reuse of the control device possible.

Figure 2:
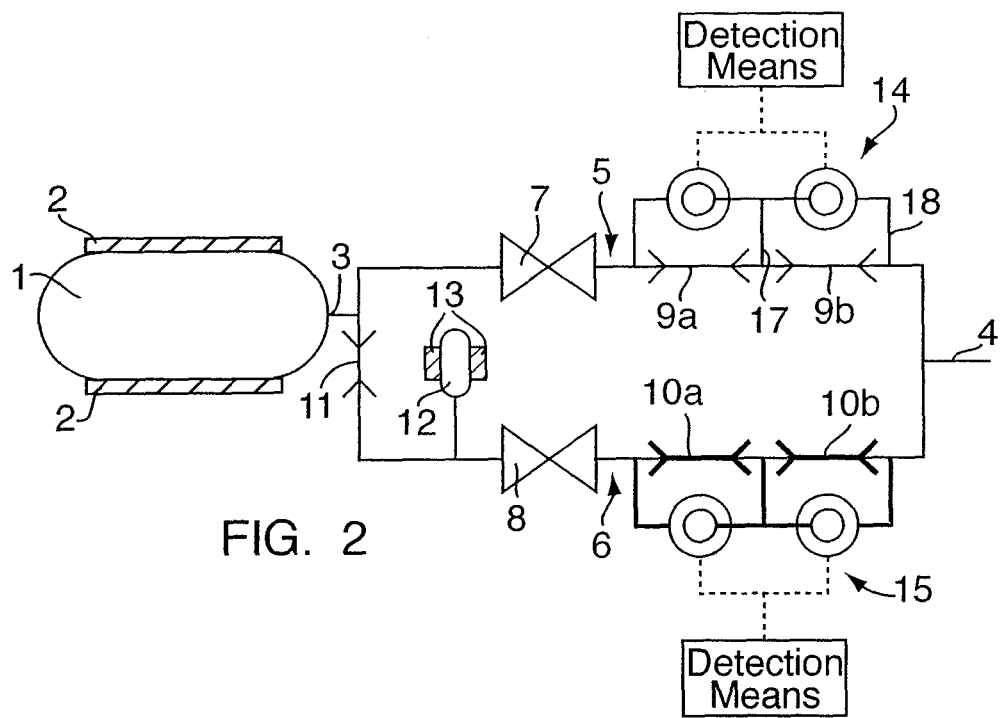
FIG. 2 shows a device for administering of medication comprising flow detectors.

In FIG. 2 is shown a infusion device similar to the device of FIG. 1. In FIG. 2 each of the capillaries 9 and 10 are divided into two series connected capillaries, 9a, 9b and 10a, 10b respectively. Except from 9a, 9b, 10a and 10b all reference numbers from FIG. 1 apply to FIG. 2. The two series connected capillaries, 9a, 9b and 10a, 10b, of FIG. 2 are each supplied with a detection device 14 and 15. The detection devices 14 and 15 are identical, and only detection device 14 is to be explained in details.

Flow of medication over capillary 9a will have a pressure drop as consequence, and this pressure drop is detected between connection 16 and 17. Pressure drop over capillary 9b is detected between connection 17 and 18. The connection 16 is in fluid communication with compartment 19 in the detector device 14, see FIG. 3, the connection 17 with compartment 20 and the connection 18 with compartment 21. The compartments 19-21 are formed by lamination of to parts 22 and 23, with deflectable membranes 24 and 25 between. The structure of the surface of each of the two parts is, on the side facing the membranes 24 and 25, such that the compartments 19-21 will be formed as the lamination has taken place.

Each membrane 24 and 25 is able to deflect upwards, indicated as position 26, or downwards, indicated as position 27. Detection means is able to detect between even position, upward position and downward position, and able to detect on each membrane separately. This detection means could simply be an optical detector, which sees the direction of a deflection. A normal infusion will have a pressure drop between compartment 19 and 20, and between compartment 20 and 21, as result. Normal infusion will therefore be detected as an upward deflection of membrane 24 and a downward deflection of membrane 25.

The table below indicates all possible detections results, and the situation leading to the result.

| Membrane 24 | Membrane 25 | Situation |
| --- | --- | --- |
| Even | Even | No flow |
| Upward | Even | 9a blocked |
| Downward | Even | Error |
| Even | Upward | Back pressure |
| Downward | Upward | Back flow |
| Even | Downward | 9b blocked |
| Upward | Downward | Normal flow |
| Downward | Downward | Error |

As it may be seen from the above table the application of two capillaries and corresponding means for detecting pressure differences over said capillaries provides the advantage that blockage of each of the communication may be detected. If only one capillary with corresponding pressure detecting means is provided, blocking of the capillary may be detected as a normal functioning capillary. This is due to the fact that a pressure difference is present over a blocked capillary.

Figure 5:
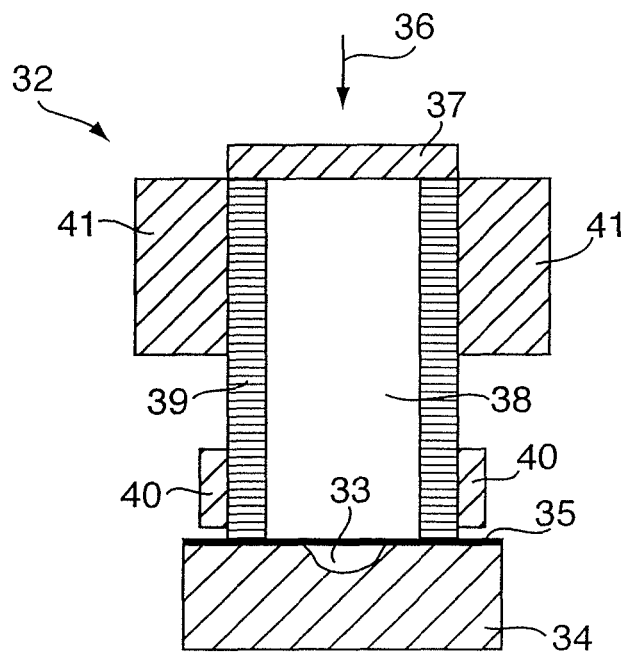
FIGS. 5 and 6 show a flow regulating device according to the second aspect of the invention.
Figure 6:
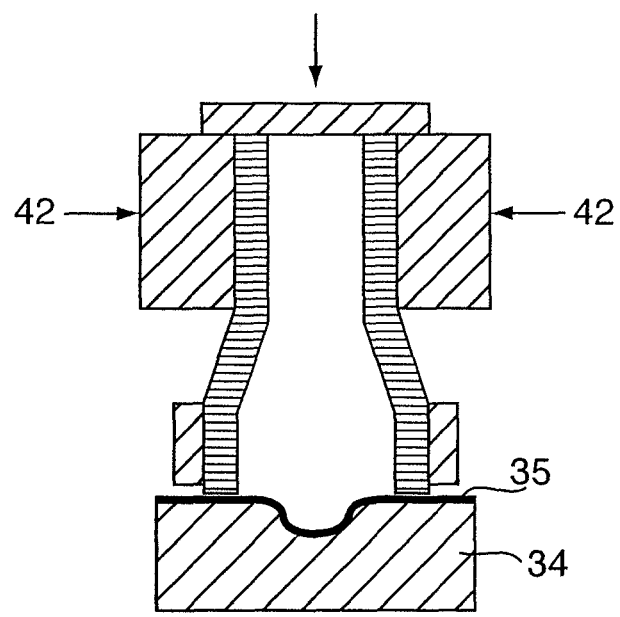

The communications 5 and 6 of FIGS. 1 and 2 consists of fluid channels, by which the storage compartment communicates with capillaries and valves. The valves 7 and 8 have the purpose of blocking one such fluid channel, which is shown at FIGS. 5 and 6. The valves, which are provided according to the second aspect of the present invention, are used in embodiments according to the first aspect of the invention.

The valve 32 of FIG. 5 is formed as a block, which is placed over a fluid channel 33, made by removing of material from a solid block 34 or by molding the block 34 with the channel 33. This solid block 34 is the infusion manifold of the infusion device of FIG. 1 or 2. Between the solid block 34 and the valve block 32 is provided a membrane, which is able to deflect into the fluid channel 33. This deflection is indicated at FIG. 6.

The valve block 32 is held against the solid block 34 by a force 36, which is acting on a solid material part 37. The valve member 38 is formed by a soft elastomer, contained within a case of a hard but deformable elastomer 39. The hard elastomer 39 is held in shape by a solid ring member 40 at the lower end, and by a moveable ring member 41 at the upper end. As a force 42 is applied to the ring member 41, the hard elastomer 39 is deformed, and the soft elastomer 38 is pressed towards the membrane 35 and into the fluid channel 33. Fluid passage is hereby prevented, as the valve member is closed.

Figure 7:
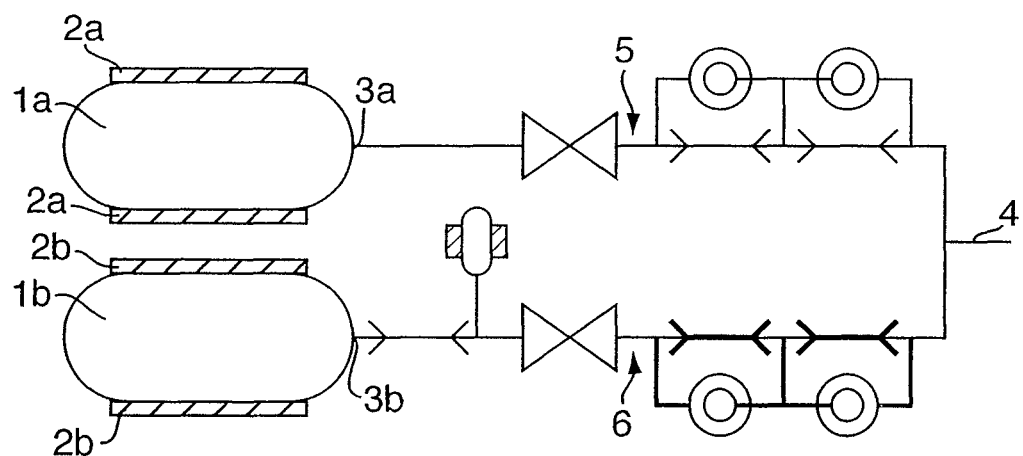
FIG. 7 shows an embodiment wherein medication is discharged from two separate compartments.

In FIG. 7 an infusion device like that of FIG. 2 is shown, but with the medication contained in two compartments, 1a and 1b. Each of the two compartments 1a and 1b are supplied with a elastomer pressure jacket 2a and 2b, and have a separate outlet 3a and 3b. The medication discharged from outlet 4 through communication 5 can hereby be different from the medication discharged from outlet 4 through communication 6. For diabetic patient, the basal rate of infusion could be with one type of insulin, and the bolus rate of infusion could be with a more power full or with a faster acting type of insulin, whereby a detected drop in the glucose level for the patient quickly could be compensated with infusion of a bolus rate.

Figure 4:
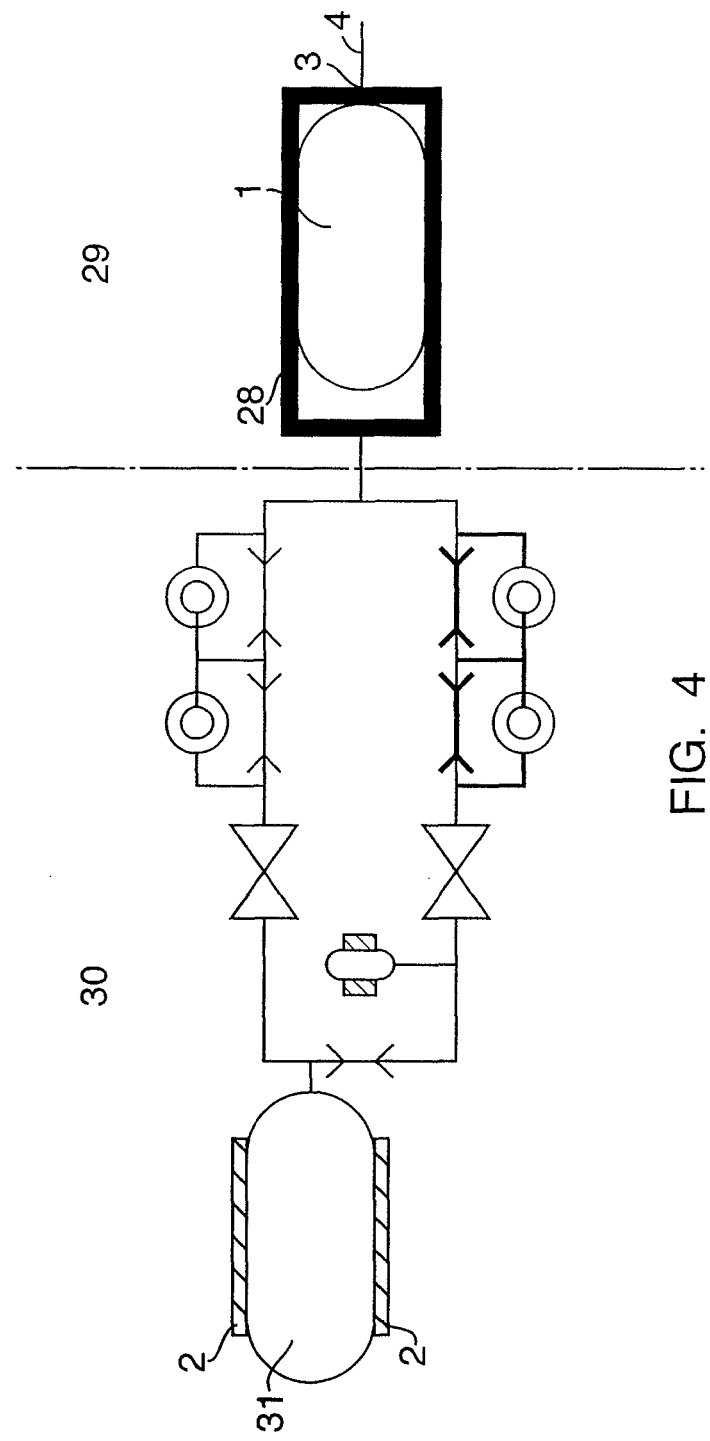
FIG. 4 shows a principal embodiment of the invention, where the medication itself is contained separate from the infusion control system.

In FIGS. 1, 2 and 7 an infusion device where the medication itself is forced through capillaries, valves and pressure variations has been shown. Some medications consist of molecules with a very sensitive structure, i.e. insulin. Those medications may be too sensitive to cope with the influences from the infusion device of FIGS. 1 and 2. In FIG. 4 however, an infusion device, having a storage compartment 1 for medication, and being in connection with an outlet 4 from the device, is shown. The storage compartment 1 is made as a sealed bag with an outlet 3, where the medication can be discharged from the bag simply by adding a external force to the bag. This external force is applied by pressurising the container 28.

Controlling the pressure in the container 28 controls the rate of infusion of medication from compartment I, and medication is therefore only contained in a small part of the infusion device, this part being indicated as position 29. Position 30 indicates the part of the infusion device for pressurising the container 28, and is the device shown in FIG. 2. The fluid in compartment 31 is not a medication, but a suitable fluid for pressurising the container 28 e.g. a saline solution. Apart from that, the function of device part 30 is similar to that of FIG. 2, and shall therefore not be described further.

Figure 3:
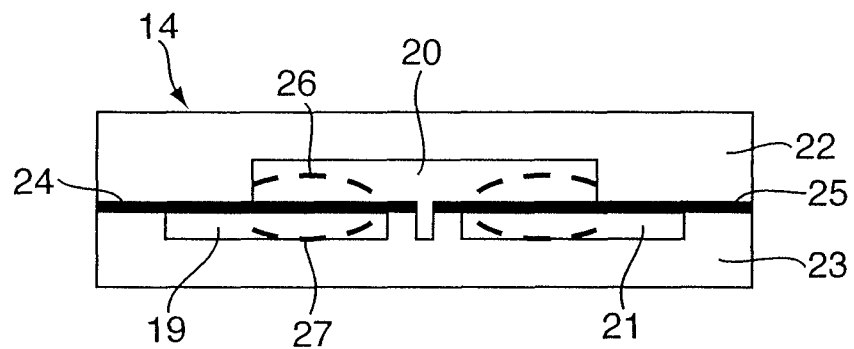
FIG. 3 shows a flow detector according to the first aspect of the invention.
Figure 8:
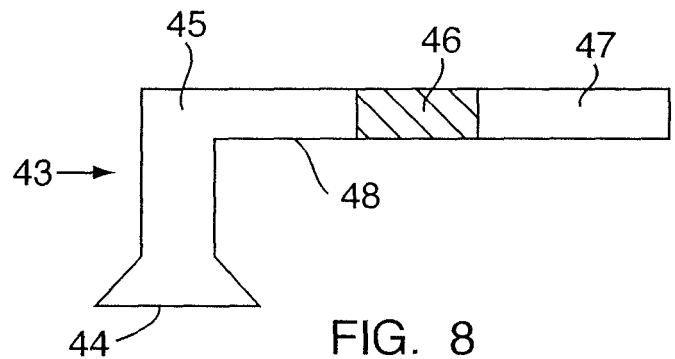
FIG. 8 shows a embodiment of a pressure detection means, and FIG. 9 A principal view of a flow detector, showing different possible detecting results in picture A-E.

FIG. 8 shows an alternative pressure detecting device 43 to that of FIG. 3. A membrane 44 seals a pipe-shaped element 48, whereby a closed compartment inside the pipe-shaped element exists. One part 45 of the closed compartment is filled with a liquid, and another part 47 is filled with air. A plunger element 46 seals the air-part 47 from the liquid part 45, and pressure acting on the membrane 44 will thus move the plunger element 46, until a force equilibrium between membrane 44 and air-part 47 arises. Detecting the movement of the plunger element 46 will therefore correspond to detecting the pressure acting on the membrane.

The air-part 47 could be formed by a sealed bellow, whereby leaking of air into the liquid-part 45 is prevented. It could also be formed simply by a spring element, whereby only leaking of liquid into the spring-part 47 is to be prevented. Of importance is only that liquid-part 45 is movable within certain limitations.

The plunger element could be a second liquid, with different colour than and not miscible with the liquid-part 45.

Hereby is the interface between the two liquids detectable, and will move due to pressure variations on the membrane 44. A sealing element between liquid-part 45 and air-part 47 will however still be needed, as totally filling of the pipe-shaped element 48 with liquid will make moving of the interface impossible.

Figure 9:
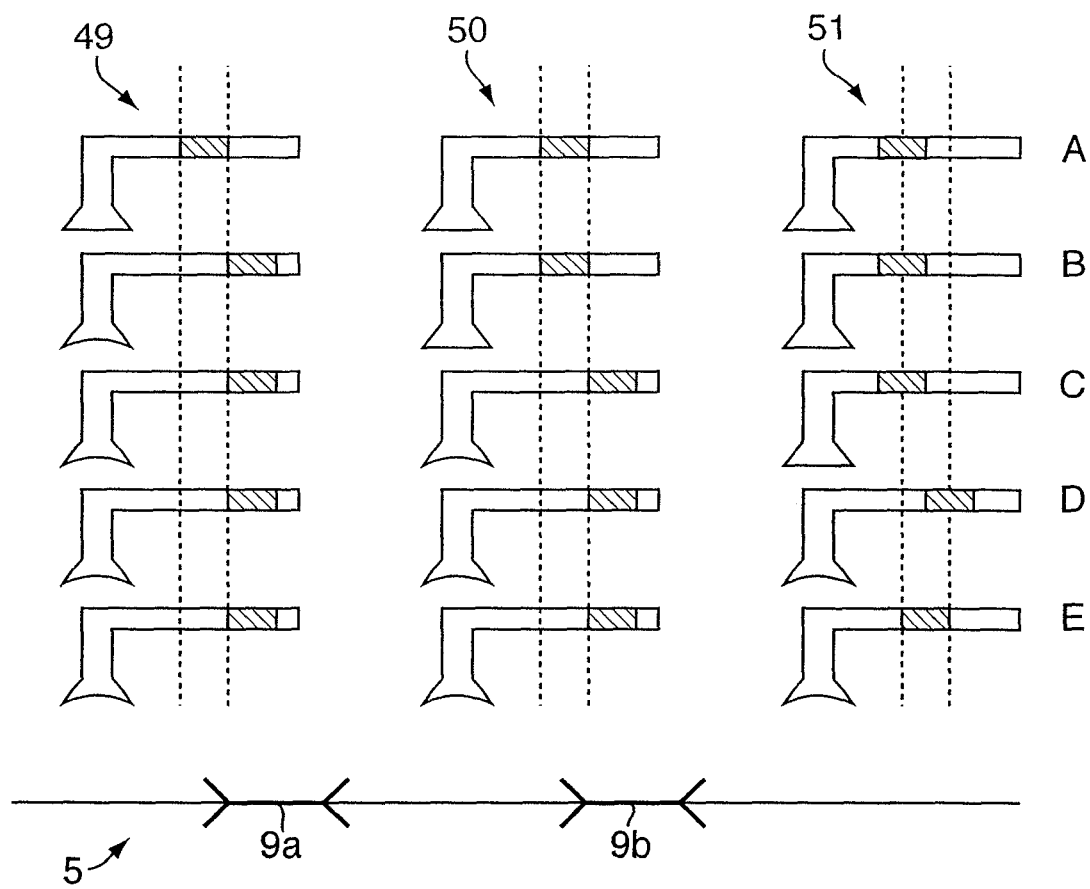

FIG. 9 indicates in picture A to E different detections results by use of the pressure detection device of FIG. 8. The infusion communication 5, with the restricting element 9a and 9b, is supplied with a total of three pressure detectors 43, indicated as detector 49, 50 and 51. The detections results will hereby be:

| Picture | Detector 49 | Detector 50 | Detector 51 | Situation |
|---|---|---|---|---|
| A | Centred | Centred | Left | No flow |
| B | Right | Centred | Left | 9a blocked |
| C | Right | Right | Left | 9b blocked |
| D | Right | Right | Right | Back pressure |
| E | Right | Right | Centred | Normal flow. |

The invention claimed is:

1. An external disposable infusion device adapted to administer a fluid based medication to a patient, the device comprising:
    a pressurized first storage compartment comprising a substantially constant pressure source;
    a first fluid path comprising two series connected capillaries in fluidic communication with the first storage compartment;
    a detection device for monitoring a pressure of a fluid in the first fluid path between the two series connected capillaries, wherein the detection device comprises a pressure sensor comprising a membrane;
    a second fluid path in fluidic communication with the first storage compartment;
    a second storage compartment in fluidic communication with the second fluid path; and
    an infusion device outlet in fluidic communication with the first fluid path and the second fluid path, wherein the first fluid path and the second fluid path form individual separate fluid paths from the first storage compartment to the infusion device outlet, wherein the first storage compartment comprises a first storage compartment outlet, and wherein each of the first fluid path and the second fluid path are in fluidic communication with the first storage compartment via the first storage compartment outlet,
    wherein the infusion device outlet is adapted to be in fluidic communication with a subcutaneous cannula in a body of the patient.

2. The infusion device of claim 1 wherein the pressure sensor further comprises a deflection detector for detecting a deflection of the membrane.

3. The infusion device of claim 1 further comprising a flow restrictor in the second fluid path upstream of the second storage compartment.

4. The infusion device of claim 1 further comprising a detection device for monitoring a flow of a fluid in the second fluid path.

5. The infusion device of claim 4 wherein the detection device comprises a pressure sensor.

6. The infusion device of claim 5 wherein the pressure sensor comprises a membrane.

7. The infusion device of claim 6 wherein the pressure sensor further comprises a deflection detector for detecting a deflection of the membrane.

8. The infusion device of claim 1 further comprising a valve in the first fluid path, upstream of the two series connected capillaries.

9. The infusion device of claim 8 wherein the valve is adjustable.

10. The infusion device of claim 1 further comprising a valve in the second fluid path, downstream of the second storage chamber.

11. The infusion device of claim 10 wherein the valve is adjustable.

12. An external disposable infusion device adapted to administer a fluid based medication to a patient, the device comprising:
    a pressurized first storage compartment comprising a substantially constant pressure source for containing a fluid wherein the first storage compartment comprises a first storage compartment outlet;
    a first fluid path comprising two series connected capillaries in fluidic communication with the first storage compartment via the first storage compartment outlet, the first fluid path comprising a detection device for monitoring a pressure of the fluid in the first fluid path between the two series connected capillaries, wherein the detection device comprises a pressure sensor comprising a membrane;
    a second fluid path in fluidic communication with the first storage compartment via the first storage compartment outlet, the second fluid path comprising a second storage compartment in fluidic communication with the second fluid path, wherein the fluid flows from the first storage compartment to the second storage compartment via the second fluid channel; and
    a common outlet in fluidic communication with the first fluid path channel and the second fluid path channel,
    wherein the common outlet is adapted to be in fluidic communication with a subcutaneous cannula in a body of the patient.

13. The infusion device of claim 12, further comprising a second pressurized source, wherein the second pressurized source defines the second storage compartment for storage of the fluid.

* * * * *